US012594136B2

(12) United States Patent
Deng

(10) Patent No.: US 12,594,136 B2
(45) Date of Patent: Apr. 7, 2026

(54) SLAVE-END GUIDEWIRE/CATHETER DRIVING APPARATUS OF INTERVENTIONAL SURGICAL ROBOT WITH FORCE DETECTION FUNCTION

(71) Applicant: SHENZHEN INSTITUTE OF ADVANCED BIOMEDICAL ROBOT CO., LTD., Guangdong (CN)

(72) Inventor: Haiyun Deng, Guangdong (CN)

(73) Assignee: SHENZHEN INSTITUTE OF ADVANCED BIOMEDICAL ROBOT CO., LTD., Shenzhen (CN)

( * ) Notice: Subject to any disclaimer, the term of this patent is extended or adjusted under 35 U.S.C. 154(b) by 788 days.

(21) Appl. No.: 17/916,098

(22) PCT Filed: Jun. 29, 2022

(86) PCT No.: PCT/CN2022/102249
§ 371 (c)(1),
(2) Date: Sep. 30, 2022

(87) PCT Pub. No.: WO2023/016120
PCT Pub. Date: Feb. 16, 2023

(65) Prior Publication Data
US 2024/0206998 A1 Jun. 27, 2024

(30) Foreign Application Priority Data

Aug. 10, 2021 (CN) .......................... 202110912557.2
Aug. 31, 2021 (CN) .......................... 202111010059.5

(51) Int. Cl.
*A61B 34/37* (2016.01)
*A61B 34/30* (2016.01)
(Continued)

(52) U.S. Cl.
CPC .............. *A61B 34/37* (2016.02); *A61B 90/06* (2016.02); *A61M 25/01* (2013.01); *A61B 2034/301* (2016.02); *A61B 2090/064* (2016.02)

(58) Field of Classification Search
CPC ........ A61B 2034/301; A61B 2090/064; A61B 34/30; A61B 34/37; A61B 34/76; A61B 90/06; A61M 25/01
See application file for complete search history.

(56) References Cited

U.S. PATENT DOCUMENTS

2015/0297864 A1* 10/2015 Kokish .................. A61B 34/37
604/95.04
2017/0165456 A1* 6/2017 Tutungi .......... A61M 25/09041
(Continued)

FOREIGN PATENT DOCUMENTS

CN 104622579 A 5/2015
CN 205175590 U 4/2016
(Continued)

OTHER PUBLICATIONS

Extended European Search Report of Counterpart European Patent Application No. 22773576.8 issued on Sep. 18, 2023.

*Primary Examiner* — Mohamed G Gabr
*Assistant Examiner* — Khoa Tan Le
(74) *Attorney, Agent, or Firm* — Hemisphere Law, PLLC

(57) ABSTRACT

Disclosed is a slave-end guidewire/catheter driving apparatus with a force detection function, disposed at a slave end of an interventional surgical robot, and configured to clamp and drive a guidewire/catheter. The apparatus includes an inner frame, a rubbing mechanism, and a first force detection module. The rubbing mechanism is disposed on the inner frame, and includes two opposite clamping sets and a driving component driving the two sets to approach or move away from each other along a first direction to clamp or unclamp the guidewire/catheter. The first force detection
(Continued)

module is at the bottom of the inner frame, and configured to detect advancement resistance in an advancement direction, perpendicular to the first direction, of the guidewire/catheter when the two sets clamp the guidewire/catheter. This application allows doctors to learn about resistance in time, which increases a sense of presence and improves surgery safety with high practicability and wide application.

15 Claims, 4 Drawing Sheets

(51) Int. Cl.
    *A61B 90/00*      (2016.01)
    *A61M 25/01*      (2006.01)

(56)               References Cited

U.S. PATENT DOCUMENTS

| | | |
|---|---|---|
| 2018/0353250 A1 | 12/2018 | Fournier et al. |
| 2021/0236217 A1 | 8/2021 | Sharon et al. |

FOREIGN PATENT DOCUMENTS

| | | | |
|---|---|---|---|
| CN | 107374739 A | 11/2017 | |
| CN | 107961077 A | 4/2018 | |
| CN | 112104573 A | 12/2020 | |
| CN | 112137725 A | 12/2020 | |
| CN | 109157287 B | 4/2021 | |
| CN | 215874930 U | 2/2022 | |
| WO | WO-2018176458 A1 * | 10/2018 | ........ A61M 25/0116 |

* cited by examiner

SLAVE-END GUIDEWIRE/CATHETER DRIVING APPARATUS OF INTERVENTIONAL SURGICAL ROBOT WITH FORCE DETECTION FUNCTION

CROSS-REFERENCE TO RELATED APPLICATIONS

This application claims priority to Chinese Patent Application No. 202110912557.2, filed on Aug. 10, 2021 and entitled "SLAVE-END GUIDEWIRE/CATHETER DRIVING APPARATUS OF INTERVENTIONAL SURGICAL ROBOT WITH FORCE DETECTION FUNCTION", and claims priority to Chinese Patent Application No. 202111010059.5, filed on Aug. 31, 2021 and entitled "SLAVE-END GUIDEWIRE/CATHETER DRIVING APPARATUS OF INTERVENTIONAL SURGICAL ROBOT WITH FORCE DETECTION FUNCTION", which are incorporated herein by reference in their entireties.

TECHNICAL FIELD

The present invention relates to the field of medical instrument and robot apparatuses, and in particular, to a slave-end guidewire/catheter driving apparatus of an interventional surgical robot with a force detection function.

BACKGROUND

Interventional therapy is a minimally invasive treatment with modern high-tech means, that is, under the guidance of medical imaging equipment, precision instruments such as special catheters and guidewires are introduced into a human body to diagnose and locally treat internal diseases.

Interventional therapy uses digital technologies to expand a doctor's field of vision, and the doctor's hands are extended with the help of catheters and guidewires. Its incision (puncture point) is only a size of a grain of rice. Without cutting through human tissue, interventional therapy can treat many previously untreatable diseases that must be treated by surgery or has a poor curative effect by internal medicine, such as tumors, hemangiomas, and various bleeding. Interventional therapy has characteristics of no operation, small traumas, quick recovery, and a good effect, and becomes a development trend of future medicine.

In vascular interventional surgery, a doctor needs to be exposed to X-ray radiation for a long time. Therefore, in engineering, a master-slave vascular interventional surgical robot for remote operation has been developed. The master-slave vascular interventional surgical robot can work in a strong radiation environment, and in this case, the doctor controls a slave end at a master end outside the radiation environment.

In a process of advancing, retreating, or rotating the guidewire (or catheter), the surgical robot needs to be driven by a corresponding transmission mechanism. However, a transmission mechanism of an existing surgical robot has no force detection function. When operating at the master end, the doctor cannot sense resistance of the guidewire or catheter when it moves in the human body, a sense of presence is not strong, and it is easy to forcibly perform an operation, causing harm to a patient.

SUMMARY

Based on this, it is necessary to provide a novel slave-end guidewire/catheter driving apparatus of an interventional surgical robot with a force detection function in view of disadvantages in the prior art.

A slave-end guidewire/catheter driving apparatus of an interventional surgical robot with a force detection function is provided, and is disposed at a slave end of an interventional surgical robot, and configured to implement clamping and driving of a guidewire/catheter. The apparatus includes an inner frame, a rubbing mechanism, and a first force detection module. The rubbing mechanism is disposed on the inner frame, and the rubbing mechanism includes two oppositely arranged clamping sets and a driving component. The driving component drives the two clamping sets to move close to or away from each other along a first direction to clamp or unclamp the guidewire/catheter. The first force detection module is disposed at the bottom of the inner frame, and when the two clamping sets clamp the guidewire/catheter, the first force detection module is configured to detect advancement resistance in an advancement direction, perpendicular to the first direction, of the guidewire/catheter.

Further, the apparatus further includes an auxiliary module cooperating with the first force detection module in detecting the advancement resistance.

Further, the auxiliary module includes a slide rail and a slider disposed slidable on the slide rail, the slider is fixed to the bottom of the inner frame, and an installation direction of the slide rail is parallel to the advancement direction of the guidewire/catheter.

Further, the apparatus further includes a second force detection module configured to detect clamping force of the two clamping sets that acts on the guidewire/catheter.

Further, the first force detection module includes a first force measurement sensor installed at the bottom of the inner frame, a fixing base, and an elastic member located between the first force measurement sensor and the fixing base.

Further, the elastic member is a compression spring extending along the advancement direction of the guidewire/catheter, and its two ends are respectively abutted between the first force measurement sensor and the fixing base.

Further, the first force measurement sensor and the compression spring are located inside the fixing base.

Further, the driving component includes two first underframes and a driver that drives the two first underframes to move along the first direction, and the two clamping sets are respectively installed on the two first underframes.

Further, the driving component further includes a first linkage wheel connected to both the two first underframes, the two first underframes are arranged opposite to each other, and the first linkage wheel is located between the two first underframes.

Further, both inner sides of the two first underframes are provided with teeth, an outer surface of the first linkage wheel is provided with teeth, and the first linkage wheel is engaged with both the first underframes of the two clamping sets through the teeth.

Further, the second force detection module includes a second force measurement sensor installed on one of the two first underframes and a connecting plate connecting the driver and the second force measurement sensor in the first direction, and when the two clamping sets unclamp the guidewire/catheter, the connecting plate enables the second force measurement sensor to generate a predetermined pressure; or when the two clamping sets clamp the guidewire/catheter, the first underframe drives the second force measurement sensor to displace to change the predetermined pressure, so as to measure clamping force of the two clamping sets that acts on the guidewire/catheter.

Further, a baffle plate is disposed on the first underframe on which the second force measurement sensor is installed, and a side surface, away from the driver, of the baffle plate is provided with an assembly groove. The second force measurement sensor is disposed in the assembly groove, and the second force measurement sensor protrudes from the assembly groove. A side that is close to the first underframe and that is of the connecting plate is provided with an opening, and the opening is sleeved on the baffle plate and the second force measurement sensor.

Further, the second force measurement sensor is a pressure sensor.

Further, the inner frame is further provided with two bearings, the two first underframes of the driving component are respectively disposed on the two bearings, and each of the first underframes is slidable on a corresponding bearing along the first direction.

Further, the driver is an electromagnetic driver.

Further, the driving apparatus further includes a rack, and the rack is sleeved on an outer side of the inner frame and the rubbing mechanism to isolate the rubbing mechanism from the outside.

In summary, according to the slave-end guidewire/catheter driving apparatus of an interventional surgical robot with a force detection function in the present invention, the first force detection module and the second force detection module are disposed, and the first force detection module and the second force detection module collect, respectively from the first direction and the second direction, the clamping force acting on the guidewire/catheter and the resistance encountered when the guidewire/catheter enters a patient's body. A system controller feeds the information back to a master end, so that a doctor can learn about resistance information in time, which increases a sense of presence and improves surgery safety with strong practicability and high promotion value.

DESCRIPTION OF EMBODIMENTS

To make objectives, technical solutions, and advantages of the present invention more clearly, the following further describes the present invention in detail with reference to the accompanying drawings and embodiments. It should be understood that the specific embodiments described herein are merely intended to explain the present invention, but not to limit the present invention.

Figure 1:
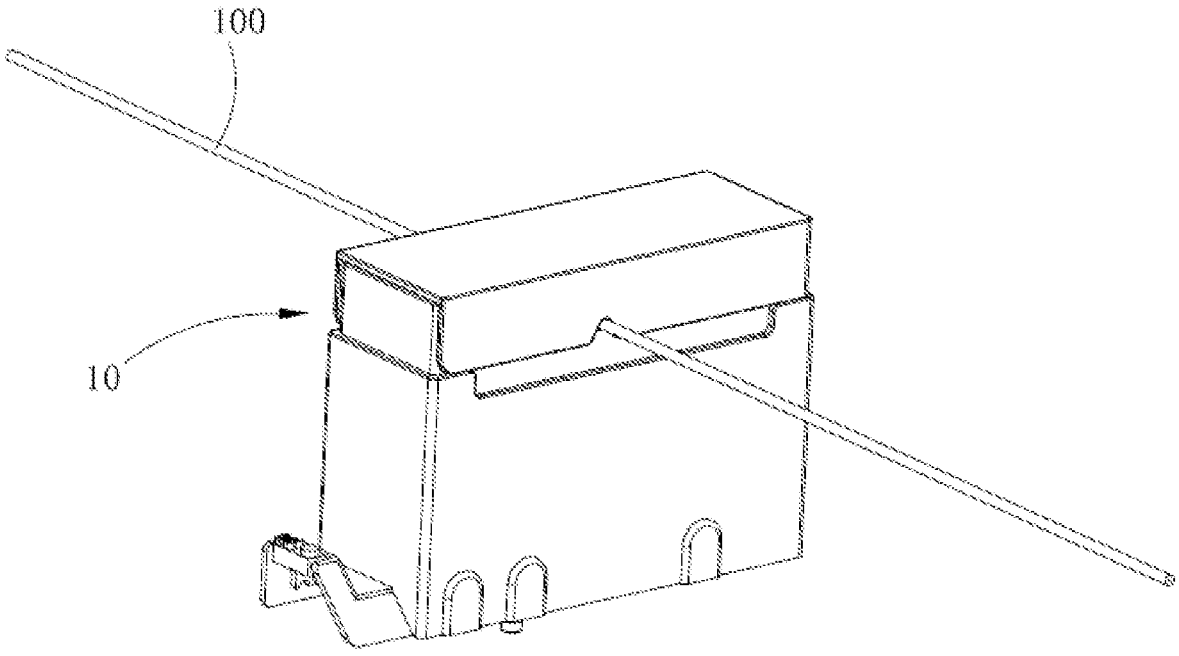
FIG. 1 is a schematic diagram of a structure of a slave-end guidewire/catheter driving apparatus of an interventional surgical robot with a force detection function according to the present invention.
Figure 2:
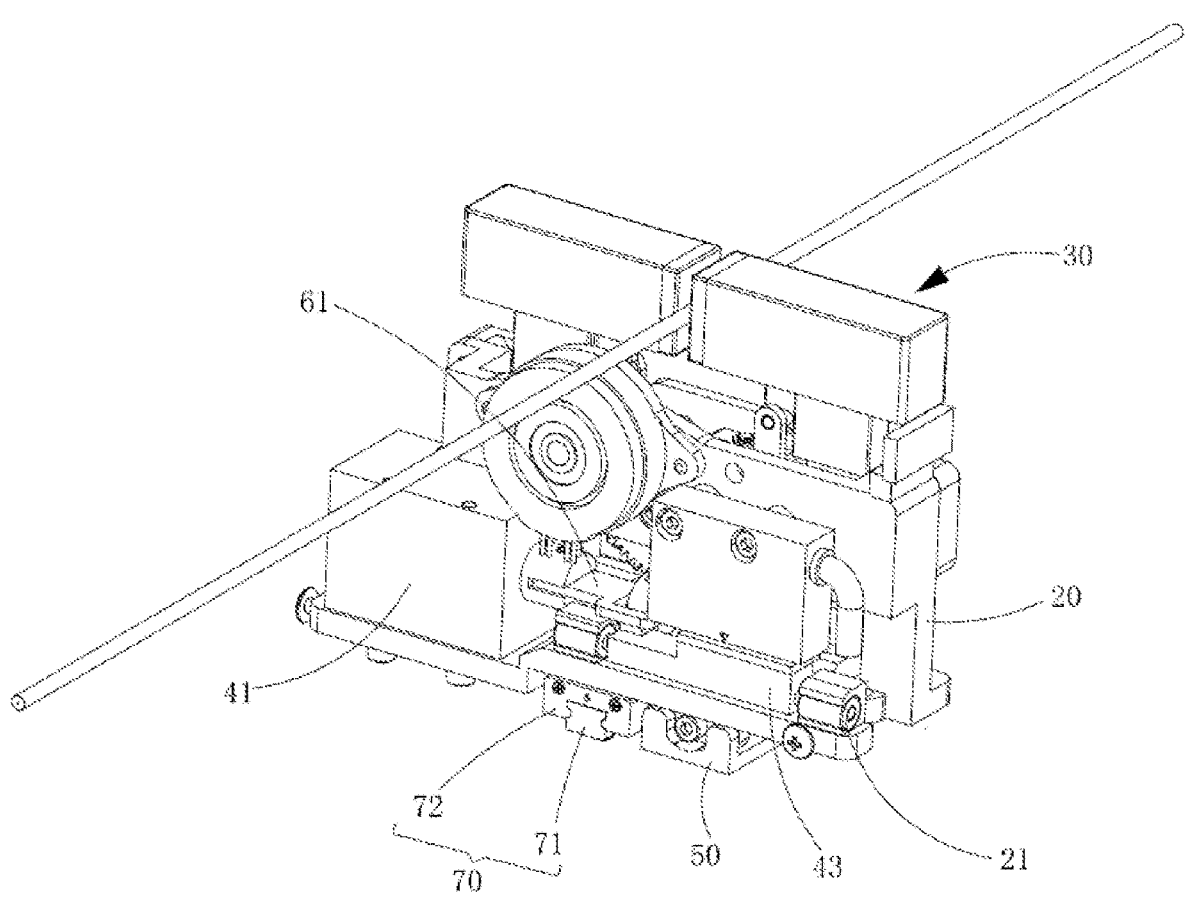
FIG. 2 is a three-dimensional diagram of the slave-end guidewire/catheter driving apparatus of an interventional surgical robot with a force detection function in FIG. 1 after a rack is removed.
Figure 3:
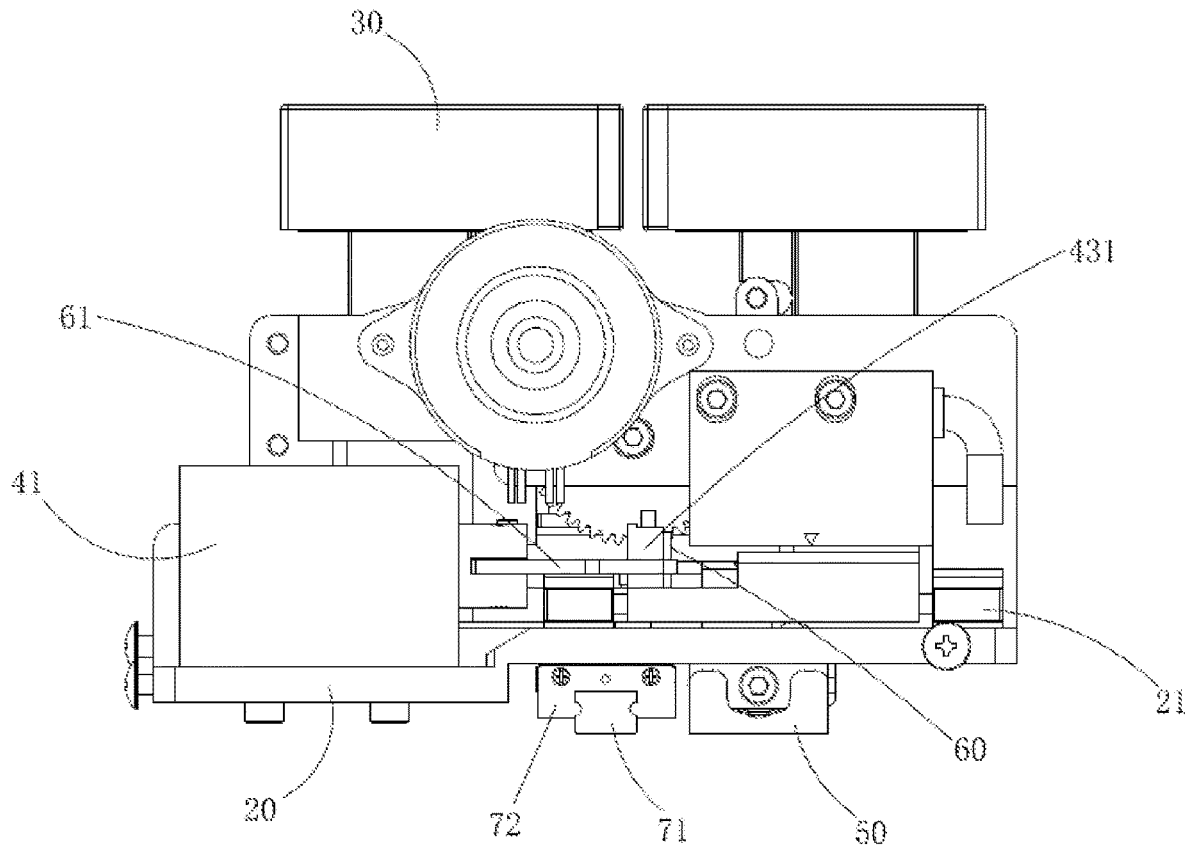
FIG. 3 is a front view of the slave-end guidewire/catheter driving apparatus of an interventional surgical robot with a force detection function in FIG. 1 after a rack is removed.
Figure 4:
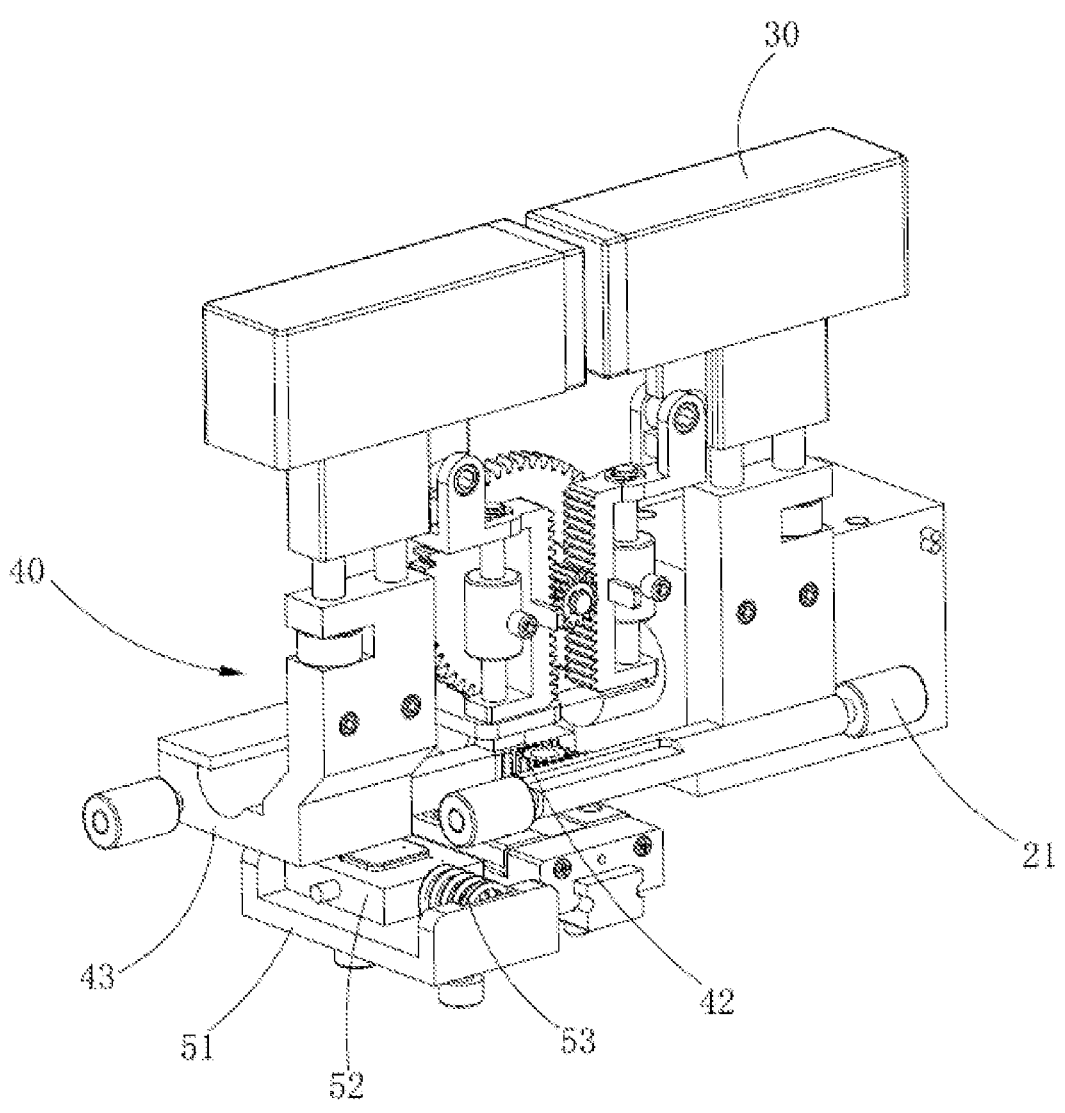
FIG. 4 is a schematic diagram of a structure of the slave-end guidewire/catheter driving apparatus of an interventional surgical robot with a force detection function in FIG. 2 after a rack and an inner frame are removed.

As shown in FIG. 1 to FIG. 4, the present invention provides a slave-end guidewire/catheter driving apparatus of an interventional surgical robot with a force detection function, which is disposed at a slave end of an interventional surgical robot, and pushes a slender medical instrument (guidewire or catheter) 100 to perform a clamping or unclamping operation.

The slave-end guidewire/catheter driving apparatus of an interventional surgical robot with a force detection function comprises a rack 10, an inner frame 20, and a rubbing mechanism. The rubbing mechanism is disposed on the inner frame 20, and the rack 10 is sleeved on an outer side of the inner frame 20 and the rubbing mechanism to isolate the outside from the rubbing mechanism. The rubbing mechanism includes two oppositely arranged clamping sets 30 and a first driving component 40. The first driving component 40 drives the two clamping sets 30 to move close to or away from each other along a first direction. When the first driving component 40 drives the two clamping sets 30 to move close to each other in the first direction, the two clamping sets 30 clamp the guidewire/catheter.

The first driving component 40 includes two first underframes 43 installed on the inner frame 20, a first linkage wheel 42 connected to both the two first underframes 43, and a driver 41 that drives the two first underframes 43 to move along the first direction. The two first underframes 43 are disposed opposite to each other. The first linkage wheel 42 is disposed between the two first underframes 43, and allows the two first underframes 43 to synchronously move close to or away from each other in the first direction. Both inner sides of the two first underframes 43 are provided with teeth, an outer surface of the first linkage wheel 42 is provided with teeth, and the first linkage wheel 42 is engaged with both the first underframes 43 of the first driving component 40 through the teeth. Under the action of the first linkage wheel 42, the driver 41 drives both the two first underframes 43 to move in opposite directions along the first direction, to drive the two clamping sets 30 to move close to or away from each other along the first direction, so as to drive the two clamping sets 30 to perform a clamping or unclamping action. In this embodiment, the driver 41 is an electromagnetic driver.

The inner frame 20 is further provided with two bearings 21, the two first underframes 43 of the first driving component 40 are respectively disposed on the two bearings 21, and each of the first underframes 43 is slidable on a corresponding bearing 21 along the first direction.

The slave-end guidewire/catheter driving apparatus of an interventional surgical robot with a force detection function further includes a second force detection module 60 and a first force detection module 50. The second force detection module 60 comprises a second force measurement sensor installed on one of the two first underframes 43 and a connecting plate 61 connecting the driver 41 and the second force measurement sensor in the first direction. When the two clamping sets 30 unclamp the guidewire/catheter, the connecting plate 61 enables the second force measurement sensor to generate a predetermined pressure. When the two clamping sets 30 clamp the guidewire/catheter, the first underframe 43 drives the second force measurement sensor to displace to change the predetermined pressure, so as to measure clamping force of the two clamping sets 30 that acts on the guidewire/catheter. A baffle plate 431 is disposed on the first underframe 43, and a side surface, away from the driver 41, of the baffle plate 431 is provided with an assembly groove. The second force measurement sensor is disposed in the assembly groove, and the second force measurement sensor protrudes from the assembly groove. A side that is close to the first underframe 43 and that is of the connecting plate 61 is provided with an opening, and the opening is sleeved on the baffle plate 431 and the second force measurement sensor. In this embodiment, the second force measurement sensor is a pressure sensor.

When the two clamping sets 30 clamp the guidewire/catheter, the two first underframes 43 drive the second force measurement sensor to displace to change the predetermined pressure. A system controller records the change of pressure information and feeds it back to a master end at which a doctor operates, which increases a sense of presence of the doctor.

The slave-end guidewire/catheter driving apparatus of an interventional surgical robot with a force detection function further includes an auxiliary module 70. The auxiliary module 70 is configured to cooperate with the first force detection module 50 in performing force detection, and includes a slide rail 71 and a slider 72. The first force detection module 50 includes a first force measurement sensor 52 fixed to the bottom of the inner frame 20, an elastic member 53, and a fixing base 51. The fixing base 51 is fixed onto a support plate (not shown in the figure) for supporting the driving apparatus, and the slider 72 is fixed onto the bottom of the inner frame 20. The slide rail 71 is installed on the support plate (not shown in the figure) for supporting the driving apparatus, and an installation direction of the slide rail 71 is the same as an advancement direction of the slender medical instrument 100. The slider 72 and the slide rail 71 are installed in cooperation with each other. When advancement resistance in a second direction (namely, the advancement direction of the slender medical instrument 100) perpendicular to the first direction changes, the slider 72 may slide slightly on the slide rail 71 along the second direction perpendicular to the first direction. The elastic member 53 is a compression spring extending along the advancement direction of the guidewire/catheter, and its two ends are respectively abutted between the first force measurement sensor 52 and the fixing base 51. Both the first force measurement sensor 52 and the elastic member 53 are disposed inside the fixing base 51, and the first force measurement sensor 52 is fixedly installed on the bottom of the inner frame 20. An arrangement direction of the first force measurement sensor 52 and the elastic member 53 inside the fixing base 51 is the same as the second direction. Both ends of the elastic member 53 are respectively abutted between the first force measurement sensor 52 and the fixing base 51. During a process of advancement of the guidewire or catheter in the second direction, advancement resistance encountered by the guidewire or catheter drives the two clamping sets 30 and the inner frame 20 to move slightly along the slide rail 71. During a movement process, a position of the first force measurement sensor 52 also changes accordingly, and the elastic member 53 changes pressing force on the first force measurement sensor 52, which in turn causes a pressure change detected by the first force measurement sensor 52. The system controller records the pressure information change and feeds it back to the master end at which the doctor operates.

In summary, according to the slave-end guidewire/catheter driving apparatus of an interventional surgical robot with a force detection function in the present invention, the first force detection module 50 and the second force detection module 60 are disposed, and the first force detection module 50 and the second force detection module 60 collect, respectively from the first direction and the second direction, the clamping force acting on the guidewire/catheter and the resistance encountered when the guidewire/catheter enters a patient's body. A system controller feeds the information back to a master end, so that a doctor can learn about resistance information in time, which increases a sense of presence and improves surgery safety with strong practicability and high promotion value.

The foregoing embodiment merely illustrates an implementation of the present invention, and the description thereof is relatively specific and detailed, but it should not be construed as a limitation on the patent scope of the present invention. It should be noted that a person of ordinary skill in the art may make variants and improvements without departing from the concept of the present invention and the variants and improvements shall fall within the protection scope of the present invention. Therefore, the protection scope of the present invention shall be subject to the protection scope of the claims.

What is claimed is:

1. A slave-end guidewire/catheter driving apparatus of an interventional surgical robot with a force detection function, disposed at a slave end of an interventional surgical robot, and configured to implement clamping and driving of a guidewire/catheter, wherein the apparatus comprises an inner frame, a rubbing mechanism, and a first force detection module, the rubbing mechanism is disposed on the inner frame, the rubbing mechanism comprises two oppositely arranged clamping sets and a driving component, the driving component drives the two clamping sets to move close to or away from each other along a first direction to clamp or unclamp the guidewire/catheter, the first force detection module is disposed at the bottom of the inner frame, and when the two clamping sets clamp the guidewire/catheter, the first force detection module is configured to detect advancement resistance in an advancement direction, perpendicular to the first direction, of the guidewire/catheter; and wherein the apparatus further comprises a second force detection module comprising a second force measurement sensor and a connecting plate connecting the driving component and the second force measurement sensor in the first direction, wherein the second force measurement sensor is configured to detect clamping force of the two clamping sets that acts on the guidewire/catheter by measuring a pressure that is applied by the connecting plate.

2. The slave-end guidewire/catheter driving apparatus of an interventional surgical robot with a force detection function according to claim 1, further comprising an auxiliary module cooperating with the first force detection module in detecting the advancement resistance.

3. The slave-end guidewire/catheter driving apparatus of an interventional surgical robot with a force detection function according to claim 2, wherein the auxiliary module comprises a slide rail and a slider disposed slidable on the slide rail, the slider is fixed to the bottom of the inner frame, and an installation direction of the slide rail is parallel to the advancement direction of the guidewire/catheter.

4. The slave-end guidewire/catheter driving apparatus of an interventional surgical robot with a force detection function according to claim 1, wherein the first force detection module comprises a first force measurement sensor installed at the bottom of the inner frame, a fixing base, and an elastic member located between the first force measurement sensor and the fixing base.

5. The slave-end guidewire/catheter driving apparatus of an interventional surgical robot with a force detection function according to claim 4, wherein the elastic member is a compression spring extending along the advancement direction of the guidewire/catheter, and its two ends are respectively abutted between the first force measurement sensor and the fixing base.

6. The slave-end guidewire/catheter driving apparatus of an interventional surgical robot with a force detection function according to claim 4, wherein the first force measurement sensor and the compression spring are located inside the fixing base.

7. The slave-end guidewire/catheter driving apparatus of an interventional surgical robot with a force detection function according to claim 1, wherein the driving component comprises two first underframes and a driver that drives the two first underframes to move along the first direction, and the two clamping sets are respectively installed on the two first underframes.

8. The slave-end guidewire/catheter driving apparatus of an interventional surgical robot with a force detection function according to claim 7, wherein the driving component further comprises a first linkage wheel connected to both the two first underframes, the two first underframes are arranged opposite to each other, and the first linkage wheel is located between the two first underframes.

9. The slave-end guidewire/catheter driving apparatus of an interventional surgical robot with a force detection function according to claim 8, wherein both inner sides of the two first underframes are provided with teeth, an outer surface of the first linkage wheel is provided with teeth, and the first linkage wheel is engaged with both the first underframes of the two clamping sets through the teeth.

10. The slave-end guidewire/catheter driving apparatus of an interventional surgical robot with a force detection function according to claim 7, wherein the second force measurement sensor is installed on one of the two first underframes and the connecting plate connecting the driver and the second force measurement sensor in the first direction, and when the two clamping sets unclamp the guidewire/catheter, the connecting plate enables the second force measurement sensor to generate a predetermined pressure; or when the two clamping sets clamp the guidewire/catheter, the first underframe drives the second force measurement sensor to displace to change the predetermined pressure, so as to measure clamping force of the two clamping sets that acts on the guidewire/catheter.

11. The slave-end guidewire/catheter driving apparatus of an interventional surgical robot with a force detection function according to claim 10, wherein a baffle plate is disposed on the first underframe on which the second force measurement sensor is installed, a side surface, away from the driver, of the baffle plate is provided with an assembly groove, the second force measurement sensor is disposed in the assembly groove, the second force measurement sensor protrudes from the assembly groove, a side that is close to the first underframe and that is of the connecting plate is provided with an opening, and the opening is sleeved on the baffle plate and the second force measurement sensor.

12. The slave-end guidewire/catheter driving apparatus of an interventional surgical robot with a force detection function according to claim 10, wherein the second force measurement sensor is a pressure sensor.

13. The slave-end guidewire/catheter driving apparatus of an interventional surgical robot with a force detection function according to claim 7, wherein the inner frame is further provided with two bearings, the two first underframes of the driving component are respectively disposed on the two bearings, and each of the first underframes is slidable on a corresponding bearing along the first direction.

14. The slave-end guidewire/catheter driving apparatus of an interventional surgery robot with a force detection function according to claim 7, wherein the driver is an electromagnetic driver.

15. The slave-end guidewire/catheter driving apparatus of an interventional surgical robot with a force detection function according to claim 1, wherein the driving apparatus further comprises a rack, and the rack is sleeved on an outer side of the inner frame and the rubbing mechanism to isolate the rubbing mechanism from the outside.

* * * * *